US012793378B2

(12) United States Patent
Chan et al.

(10) Patent No.: US 12,793,378 B2
(45) Date of Patent: Nov. 10, 2026

(54) METHOD FOR RECONCEPTUALIZATION OF DEEP LEARNING-BASED TRANSLATION OF T1- WEIGHTED IMAGE TO MAGNETIC RESONANCE ANGIOGRAPHY (MRA) AND A SYSTEM FOR DEEP LEARNING-BASED TRANSLATION OF T1-WEIGHTED IMAGE TO VASCULATURE IMAGE OF A BRAIN

(71) Applicants: Hong Kong Centre for Cerebro-Cardiovascular Health Engineering Limited, Pak Shek Kok (HK); City University of Hong Kong, Kowloon Tong (HK)

(72) Inventors: Kannie Wai Yan Chan, Pak Shek Kok (HK); Abdul-Mojeeb Olabisi Ilyas, Pak Shek Kok (HK); Jianpan Huang, Pak Shek Kok (HK); Rohith Saai Pemmasani Prabakaran, Pak Shek Kok (HK); Yang Liu, Pak Shek Kok (HK); Se Weon Park, Pak Shek Kok (HK)

(73) Assignees: Hong Kong Centre for Cerebro-Cardiovascular Health Engineering Limited, Pak Shek Kok (HK); City University of Hong Kong, Kowloon Tong (HK)

( * ) Notice: Subject to any disclaimer, the term of this patent is extended or adjusted under 35 U.S.C. 154(b) by 250 days.

(21) Appl. No.: 18/426,736

(22) Filed: Jan. 30, 2024

(65) Prior Publication Data

US 2025/0245956 A1 Jul. 31, 2025

(51) Int. Cl.

*G06V 10/44* (2022.01)
*A61B 5/055* (2006.01)
*G06T 3/40* (2024.01)

(52) U.S. Cl.

CPC .............. *G06V 10/44* (2022.01); *A61B 5/055* (2013.01); *G06T 3/40* (2013.01)

(58) Field of Classification Search

CPC ........... G06V 10/44; A61B 5/055; G06T 3/40; G06T 12/00; G06T 17/00; G06N 3/0455; G06N 3/0464

See application file for complete search history.

(56) References Cited

U.S. PATENT DOCUMENTS 11,699,281 B2 * 7/2023 Han ..................... G06V 10/764 382/128
11,861,501 B2 * 1/2024 Chen .................... G06N 3/0455
(Continued)

OTHER PUBLICATIONS

Glockner, J. F. et al. Non-contrast renal artery MRA using an inflow inversion recovery steady state free precession technique (Inhance): Comparison with 3D contrast-enhanced MRA. Journal of Magnetic Resonance Imaging 31, 1411-1418 (2010).
(Continued)

*Primary Examiner* — Stephen R Koziol
*Assistant Examiner* — Michael Kim Maiden
(74) *Attorney, Agent, or Firm* — Renner, Kenner, Greive, Bobak, Taylor & Weber

(57) ABSTRACT

The present invention provides an artificial intelligence engine configured to a UNet model including an encoder and a decoder that can synthesize 3D MRA and MIP of MRA using acquired single contrast MR image (T1-w MR image) for the same subject while preserving the continuity of vascular anatomy and important vascular morphological features.

19 Claims, 12 Drawing Sheets

(56) References Cited

U.S. PATENT DOCUMENTS

| | | | | |
|---|---|---|---|---|
| 12,437,391 | B2 * | 10/2025 | Nielsen | G16H 30/20 |
| 2021/0074036 | A1 * | 3/2021 | Fuchs | G06T 11/006 |
| 2021/0225027 | A1 * | 7/2021 | Wang | G06F 18/295 |
| 2025/0078290 | A1 * | 3/2025 | Xia | G06T 3/40 |

OTHER PUBLICATIONS

Olut, S., Sahin, Y. H., Demir, U. & Unal, G. Generative Adversarial Training for MRA Image Synthesis Using Multi-contrast MRI. 11121 LNCS, 147-154 (2018).

Sohail, M., Riaz, M. N., Wu, J., Long, C. & Li, S. Unpaired multi-contrast MR image synthesis using generative adversarial networks. 11827 LNCS, 22-31 (2019).

Hsu, C. Y. et al. Gap-free segmentation of vascular networks with automatic image processing pipeline. Comput Biol Med 82, 29-39 (2017).

* cited by examiner

METHOD FOR RECONCEPTUALIZATION OF DEEP LEARNING-BASED TRANSLATION OF T1- WEIGHTED IMAGE TO MAGNETIC RESONANCE ANGIOGRAPHY (MRA) AND A SYSTEM FOR DEEP LEARNING-BASED TRANSLATION OF T1-WEIGHTED IMAGE TO VASCULATURE IMAGE OF A BRAIN

TECHNICAL FIELD

The present invention relates to a system and a method for Reconceptualization of Deep Learning-Based Translation of T1-weighted image to Magnetic Resonance Angiography (MRA).

BACKGROUND

Magnetic resonance angiography (MRA) is a specialized magnetic resonance imaging sequence using inflow effect to highlight vascular features connected with maximum intensity projection (MIP) to reveal the vascular trees.

One of the existing systems uses Generative Adversarial Networks (GAN) to generate synthetic magnetic resonance angiography for data augmentation and anonymization. This deep learning-based approach translates routine single or multi-contrast MR images to MRA and requires extra maximum-intensity-projection (MIP) technology to obtain better views of organs, such as blood vessels, arteries, veins, bronchi, etc, from different directions. One major limitation associated with generating synthetic MRA from routine MR images is the discontinuity in vascular anatomy. Timing is critical in the diagnosis of cerebrovascular diseases such as stroke. It is always preferable for clinicians to conduct diagnosis in a non-invasive manner using the digitally generated cerebrovascular anatomy.

There is a preference to make MRI diagnosis of cerebrovascular disease faster and cheaper in a timely and non-invasive manner. As such, magnetic resonance is an outstanding technique for the diagnosis of cerebrovascular diseases. It will be advantageous to minimize magnetic resonance scan time while generating specific rare imaging modalities like MRA images, which highlight vascular anatomy details. With the existing technology, it is challenging to achieve this outcome as existing systems demand specialized imaging sequences underpinned by an exogenous or endogenous contrast mechanism.

SUMMARY OF THE INVENTION

In accordance with a first aspect of the present invention, there is provided a method for synthesizing MRA and MIP of MRA images using acquired single contrast MR image (T1-w MR image) by a system having at least a processor and a memory therein to execute instructions of an artificial intelligence engine configured to a UNet model stored within the memory of the system; wherein the UNet model comprises an encoder having a plurality of layer blocks, each of the layer blocks of the encoder comprising one or more convolutional layers, each of the convolution layers associating with an activation layer, and a down sampling layer;

a decoder having a plurality of layer blocks, each of the layer blocks of the decoder comprising one up-sampling layer, one or more convolutional layers, and each of the convolution layers associating with an activation layer;

a skip connection for associating with one of the layer blocks of the encoder with one of the layer blocks of the decoder at a corresponding multiscale resolution level;

wherein the encoder is adapted to extract features from the T1-w MR image for the decoder to combine outputs from the encoder and extracted image features in multiscale resolution levels through the skip connection to generate the MRA and MIP of MRA images.

In accordance with the first aspect, the decoder comprises an output layer to generate an image with a same resolution as the input image.

In accordance with the first aspect, the output layer comprises a single output convolutional layer followed by an output activation layer.

In accordance with the first aspect, the single output convolutional layer is a 1×1 convolutional layer with a stride of 1.

In accordance with the first aspect, the output activation layer is adapted to conduct hyperbolic tangent (tanh) operations.

In accordance with the first aspect, the encoder and the decoder are adapted to perform cross-sequence from a T1-w image to MRA or MIP image translation consisting of 19 convolutional layers.

In accordance with the first aspect, the encoder is adapted to receive images comprising three dimensions and one or more colour channels.

In accordance with the first aspect, one or more layer blocks of the encoder comprise a repeated implementation of two 3×3 convolution layers with 2 voxels stride over five-layer blocks.

In accordance with the first aspect, a layer block of the encoder that immediately precedes the decoder comprises a single convolution layer.

In accordance with the first aspect, a zero padding technique is implemented before each convolution layer.

In accordance with the first aspect, the activation layer is adapted to conduct a linear rectification function by one or more rectified linear units (ReLU).

In accordance with the first aspect, the down sampling comprises a 2×2×2 max-pooling operation with a stride of 2 voxels.

In accordance with the first aspect, each of the convolutional layers is adapted to process input data with a number of convolutional filters.

In accordance with the first aspect, the number of convolutional filters is doubled from a first layer block to a last layer block within the encoder.

In accordance with the first aspect, the up-sampling layer of the decoder is adapted to perform nearest-neighbour interpolation to increase image size through each layer block within the decoder.

In accordance with the first aspect, one or more convolution layers with the decoder use random initialization and unequalled kernel size.

In accordance with the first aspect, the skip connection is adapted to copied and concatenated features generated from one of the layer blocks of the encoder to one of the layer blocks of the decoder at a corresponding multiscale resolution level.

In accordance with the first aspect, the UNet model is trained with a batch size of 4.

In accordance with the first aspect, the UNet model is trained with consecutive MRA images which differed in a same manner as input images, In accordance with the first aspect, the UNet model is trained with over 100 epochs.

In accordance with a second aspect of the present invention, there is provided a system for deep learning-based translation of T1-weighted image to vasculature image of a brain comprising: a memory to store instructions and a processor to execute instructions stored within the memory; the processor to execute an artificial intelligence engine configured to a UNet model stored within the memory of the system; wherein the UNet model comprising an encoder having a plurality of layer blocks, each of the layer blocks of the encoder comprising one or more convolutional layers, each of the convolution layers associating with an activation layer, and a down sampling layer;

a decoder having a plurality of layer blocks, each of the layer blocks of the decoder comprising one up-sampling layer, one or more convolutional layers, and each of the convolution layers associating with an activation layer;

a skip connection for associating with one of the layer blocks of the encoder with one of the layer blocks of the decoder at a corresponding multiscale resolution level;

wherein the encoder is adapted to extract features from the T1-w MR image for the decoder to combine outputs from the encoder and extracted image features in multiscale resolution levels through the skip connection to generate the MRA and MIP of MRA images.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENTS

Examples of the present invention provides a computerized system or method using a novel deep-learning process to synthesize 3D maximum intensity projection (MIP) of magnetic resonance imaging (MR) image using singularly acquired T1-weighted (T1-w) MR image. In one embodiment of the present invention, there is provided a computer system 100 for executing a method comprising an artificial engine arranged with a multiple-block UNet model (or refer to the "model") 120 implemented with L2 loss function for encoding and decoding image data between each block emphasizing and minimizing the statistical feature difference between the 3D volumetric of the target and synthesized images.

Figure 2:
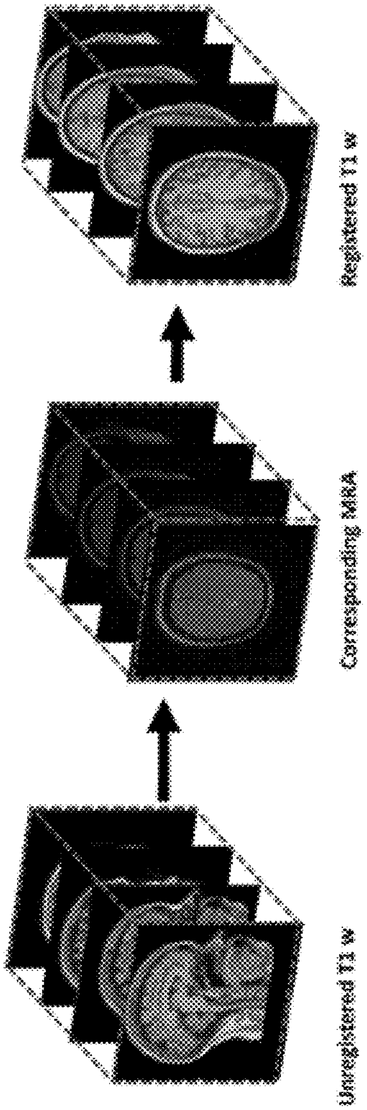
FIG. 2 is a block diagram showing a process for registration of T1-w to MRA images.
Figure 3:
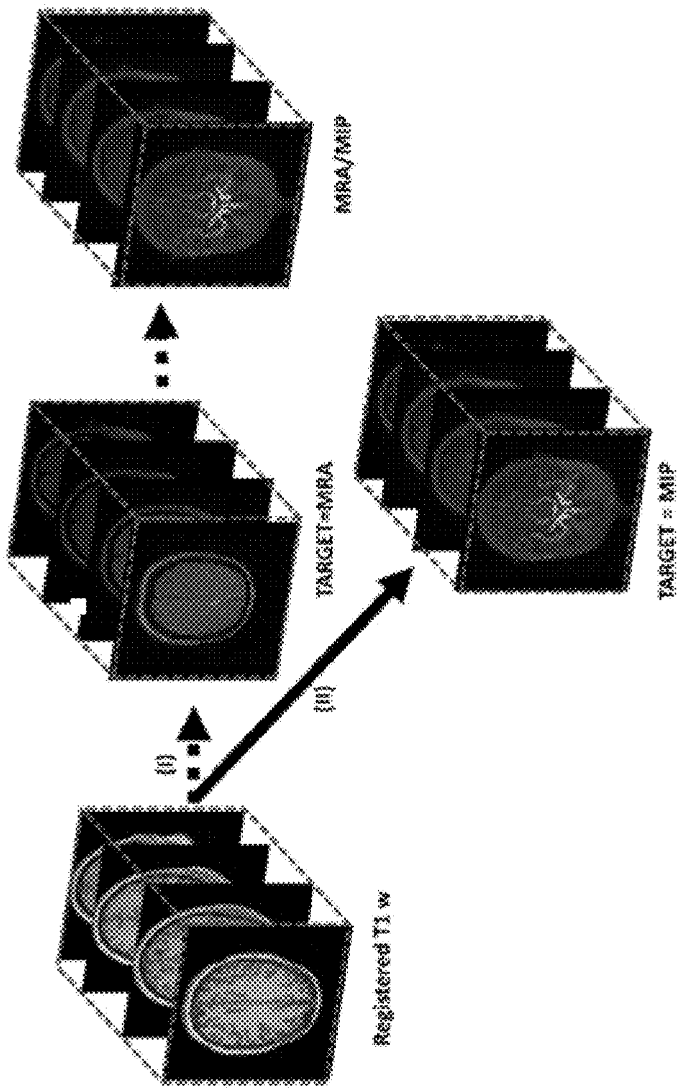
FIG. 3 is a block diagram showing a process for two pathways to translation of T1-w to MRA to MIP image.

In this embodiment, the UNet model 120 comprises an encoder 122 and a decoder 124 that can synthesize 3D MRA and MIP of MRA using acquired single contrast MR image (T1-w MR image) for the same subject while preserving the continuity of vascular anatomy and important vascular morphological features. In particular, the present invention is adapted to address the direct approach of T1-w to MIP translation, as shown in FIG. 2 and FIG. 3, which is assessed and compared against the current image T1-w to MRA to MIP translation. The present invention paves the way for easy creation of digital MIP twins with no concern about creation of defects in the vasculature.

Figure 1:
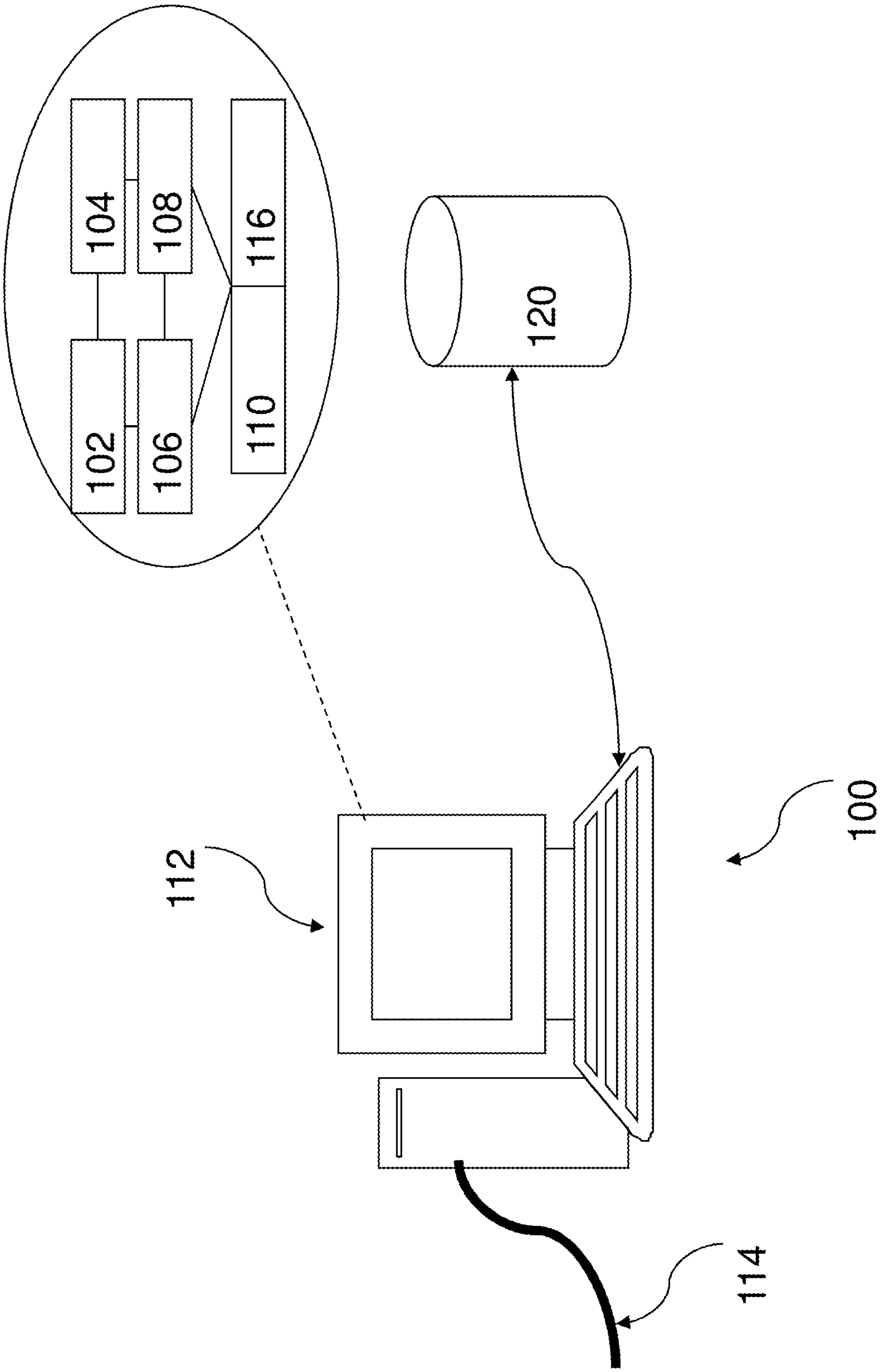
FIG. 1 is a schematic diagram of a computer server which is arranged to be implemented as a system for synthesizing MRI-MIP from MRI data in accordance with an embodiment of the present invention.
Figure 4:
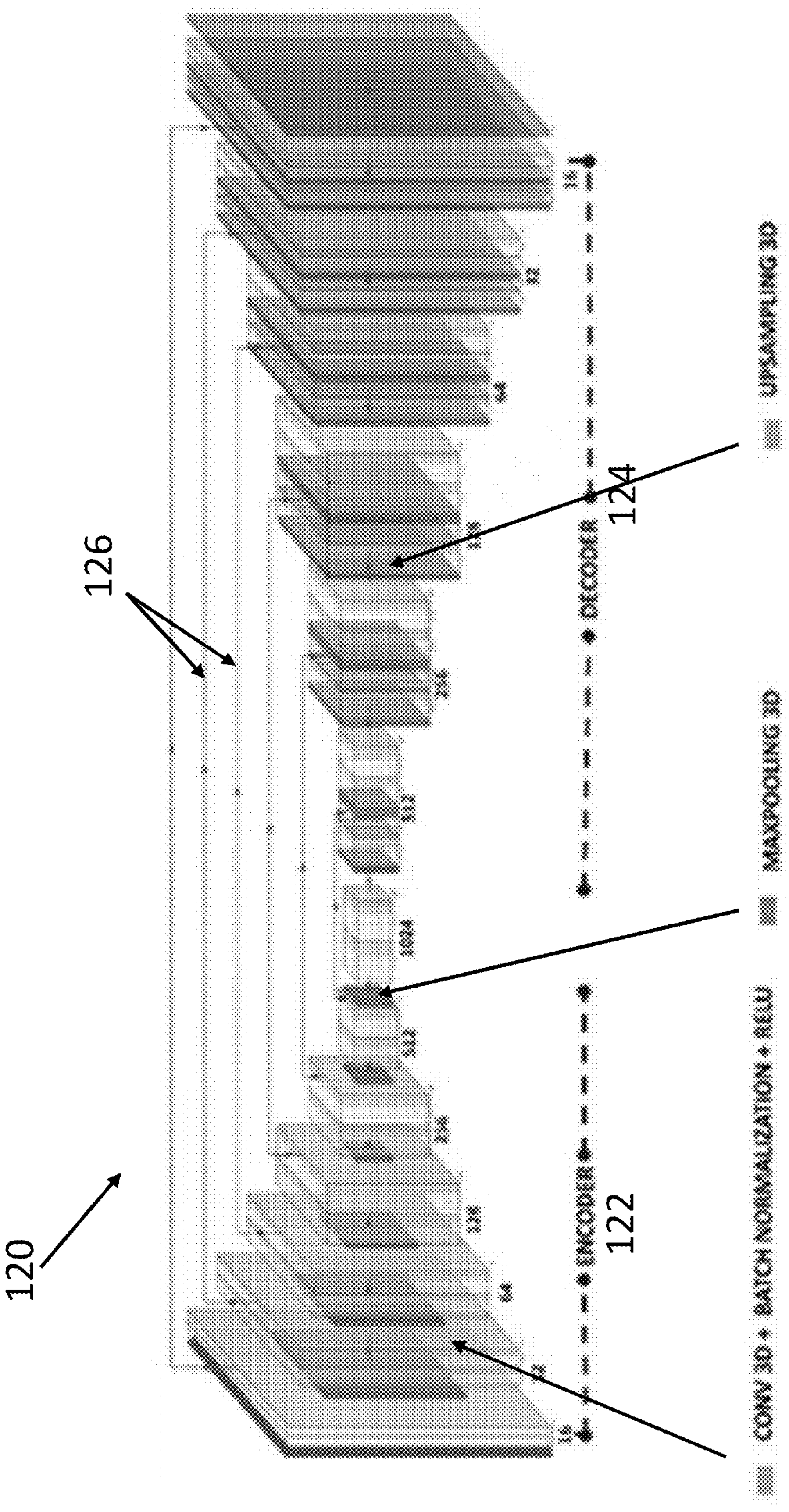
FIG. 4 is a schematic diagram of an encoder-decoder UNET architecture used for image translation in an embodiment of the present invention.

As shown in FIG. 1, there is a shown a schematic diagram of a computer system or computer server 100 which is arranged to be implemented as an example embodiment of a system for synthesizing MRA/MIP from one or more MRI images using an AI engine configured to a UNet model 120 as shown in FIG. 4. In one embodiment of the present invention, the system comprises a server 100 which includes suitable components necessary to receive, store, and execute appropriate computer instructions. The components may include a processing unit 102, including one or more Central Processors, Graphic Processing Unit (GPUs) or Tensor Processing Unit (TPUs) for tensor or multi-dimensional array calculations or manipulation operations, read-only memory (ROM) 104, random access memory (RAM) 106, and input/output devices such as disk drives 108, input devices 110 such as an Ethernet port, a USB port, etc. Display 112 such as a liquid crystal display, a light emitting display, or any other suitable display and communications links 114. The system 100 may include instructions that may be included in ROM 104, RAM 106, or disk drives 108 and may be executed by the processing unit 102. There may be provided a plurality of communication links 114 which may variously connect to one or more computing devices such as a server, personal computers, terminals, wireless or handheld computing devices, and edge computing devices. At least one of a plurality of communications links may be connected to an external computing network through a telephone line or other type of communications link.

The server 100 may include storage devices such as a disk drive 108 which may encompass solid state drives, hard disk drives, optical drives, magnetic tape drives, or remote or cloud-based storage devices. The server 100 may use a single disk drive or multiple disk drives, or a remote storage service 120. The server 100 may also have a suitable operating system 116 which resides on the disk drive or in the ROM of the server 100.

The computer or computing apparatus may also provide the necessary computational capabilities to operate or to interface with an AI Engine configured to a UNet model 120 as shown in FIG. 4. The AI engine may be implemented locally, or it may also be accessible or partially accessible via a server or cloud-based service. In one embodiment of the present invention, the system 100 is implemented as a 64-bit Linux system with an Intel Core and 164 GB RAM using Kera's API with TensorFlow (version 2.8) as the backend in Python (version 3.9; Python Software Foundation), although as it will be appreciated by a person skilled in the art, alternative hardware may also be used.

In one embodiment, there is provided a system 100 comprising: a memory 104, 106 to store instructions and a processor or processing unit 102 to execute instructions stored within the memory. The processing unit or processor 102 is adapted to execute an artificial intelligence engine configured to a UNet model 120 stored within the memory 104, 106.

The UNet model 120 comprises an encoder 122 having a plurality of layer blocks, a decoder 124 having a plurality of layer blocks, and skip connections 126. Each of the layer blocks of the encoder 122 comprises one or more convolutional layers and a down sampling layer. Each of the convolution layers is associated with an activation layer. Each of the layer blocks of the decoder comprises one up-sampling layer, one or more convolutional layers, and each of the convolution layers is associated with an activation layer. Each skip connection 126 is associated with one of the layer blocks of the encoder 122 with one of the layer blocks of the decoder 124 at a corresponding multiscale resolution level. The encoder 122 is adapted to extract larger sets of low to high-level features in the multiscale resolution levels from the T1-w MR image for the decoder 124 to combine outputs from the encoder and extracted image features in multiscale resolution levels through the skip connection to generate the MRA and MIP of MRA images. In one preferred embodiment, a batch normalization operation is carried out before passing data from a convolution layer to the activation layer.

The encoder is adapted to receive images comprising three dimensions voxels and one or more color channels. In one embodiment, one or more layer blocks of the encoder 122 comprise a repeated implementation of two 3×3 convolution layers with 2 voxels stride over five-layer blocks. The last layer block of the encoder 122 that immediately precedes the decoder 124 comprises a single convolution layer. Zero padding technique is implemented before each convolution layer. The activation layer is adapted to conduct a linear rectification function by one or more rectified linear units (ReLU). In one embodiment, the down sampling comprises a 2×2×2 max-pooling operation with a stride of 2 voxels. Each of the convolutional layers is adapted to process input data with a number of convolutional filters and the number of convolutional filters is doubled from a first layer block to a last layer block within the encoder.

The encoder 122 and the decoder 124 are adapted to perform cross-sequence from a T1-w image to MRA or MIP image translation consisting of 19 convolutional layers.

The output comprises a single 1×1 output convolutional layer with a stride of 1 followed by an output activation layer of hyperbolic tangent (tanh) operations to generate an image with a same resolution as the input image.

The up-sampling layer of the decoder is adapted to perform nearest-neighbor interpolation to increase image size through each layer block within the decoder. One or more convolution layers with the decoder use random initialization and unequalled kernel size.

The skip connection 126 is adapted to copied and concatenated features generated from one of the layer blocks of the encoder to one of the layer blocks of the decoder at a corresponding multiscale resolution level.

Preferably, the UNet model 120 of an embodiment of the present invention is trained with a batch size of 4, with consecutive MRA images which differed in a same manner as input images, and with over 100 epochs.

Magnetic resonance imaging (MRI) has emerged as one of the most powerful diagnostic tools in radiology clinics for evaluating and examining patients for cerebrovascular diseases. The strengths of MRI are its ability to provide cross-sectional images of anatomical regions in an arbitrary plane and soft-tissue contrast.

MRI is founded on the basic physics of nuclear magnetic resonance imaging (NMR) by exploiting the nuclear spin energy transition of hydrogen atoms in water and fat of body tissues. patient motion and requires excessively long scan time.

Although MRA is needed for quick diagnosis of second disease-causing disability and death worldwide, there are several practical and clinical concerns, which include the likely use of contrast agents for patients, increase in acquisition and processing time, and diagnostic cost. Consequently, some doctors may be reluctant to recommend or commission MRA for clinical examinations unless there is a strong case for retrospective inspection of the vasculatures or during endovascular concerns.

The rapid growth of artificial intelligence (AI) and its availability to more users make it possible for one embodiment of the present invention to synthesize intra- and inter-modality medical images with deep learning algorithms. One image-to-image translation approach has been employed to generate synthesized MRA images from every other single image modality. Another approach has been employed to generate synthesized MRA images from multi-input employing includes primary structural imaging sequences (T1-w and T2-w MRI), or T1, T2, PD-w images. However, these existing systems rely on computationally expensive generative adversarial network (GAN). Some employed U-NET AI models for image segmentation which can derive local and global features from input images, but it was not conceived to be used for synthesizing MRA images.

For the existing MRA image synthesis systems, the target output has been MRA images, which require a maximum intensity projection (MIP) algorithm using logic and probability to display vascular data of interest known as MIP-MRA. The MIP-MRA is essential to perform a topological analysis of the cerebrovascular. Existing MRA/MIP-MRA image synthesis systems suffer from creating unwanted defects in the synthetic images, such as artificial gaps introduced by finite image slicing sequence creating tree dysconnectivity, artefacts during translation overlapping, and sensitivity to variation in input image contrast to noise ratio, even though ongoing research studies have focused on the development of problem-free algorithms.

The present invention disclosed a novel and inventive AI engine to process and generate virtual vascular MRA images from singularly routine MRI scan images early on. The AI engine of one embodiment of the present invention is configured to comprise a UNET-based model to synthesize MIP-MRA images from a T1-w MRI contrast sequence. In this way, the present invention can directly translate routine MRI contrast to MIP-MRA image sequence.

Considering the clinical ramifications of vascular problems and the sensitivity of time in diagnosing cardiovascular disease (CVD), it is advantageous for the present invention to provide a system or method that is adapted to generate a visual presentation efficiently for clinicians to make early detection. It is also advantageous for the present invention to provide a system or method that is adapted to reduce clinical time wastage by avoiding (i) multistep processing of MRA images and (ii) acquisition of multi-contrast MR image acquisition used to obtain MRA images.

Model Architecture

In another embodiment of the present invention, there is provided a method comprises the implementation of a UNet model 120 stored in the memory of a computing system 100. The UNet model 120 comprises an encoder 122 and a decoder 124 with skip connections 126. The encoder 122 down samples the input images to extract larger sets of low to high-level features, while the decoder 124 combines the output from the encoder and extracted image features in multiscale resolution levels to generate the MRA-based target images output through an up-sampling process. Skip connections 126 are added between the reflecting layers in the encoder 122 and the decoder 124 network to speed up information transmission between input and output 3D image flows. This helps to learn matching features for the corresponding mirrored layers.

Referring to FIG. 4, there is illustrated an embodiment of an UNet model 120 implemented in one example embodiment of the present invention to perform cross-sequence from T1-w to MRA or MIP image translation consists of an odd number of convolutional layers. In another embodiment of the present invention, the UNet model 120 may comprise 19 convolutional layers.

In one embodiment of the present invention, the input image is normalized into 128×128×64 voxels and one channel (grayscale image). However, the UNet model 120 is can be adapted to process input image with a much higher resolution. The encoder 122 consists of a repeated implementation of two convolution layers of 3×3 kernels with 2 voxels stride over five-layer blocks, except for the last block, one convolutional layer. Zero padding was used before convolution to maintain the resolution of extracted deeper feature maps matching the resolution of the input feature maps. A layer block in the encoder 122 may comprise a first convolutional layer followed by a rectified linear unit (ReLU) activation layer and a 2×2×2 max-pooling operation with a stride of 2. Alternatively, a layer block in an encoder 122 may comprise two or more convolutional layers wherein each of which is followed by a rectified linear unit (ReLU) activation layer, and a 2×2×2 max-pooling operation with a stride of 2. Using a ReLU nonlinear transfer function between the hidden convolutional layers has the advantage of computational simplicity and representational sparsity, providing capabilities for better solutions and thereby not suffering from a vanishing gradient.

In the UNet model 120 of an embodiment of the present invention, the max-pooling operation implemented after the activation layer is adapted to reduce the spatial size of the image feature map by a factor of 2, decreasing the computational cost and saving memory. The number of convolutional filters doubles, from 16 in the first block to 1024 in the last block. This permits the network to learn the hierarchical relationships over a sizeable receptive field of the MR image.

The decoder 124 of an embodiment of the present invention is configured as a reflected version of the encoder 122. One difference between the encoder 122 and the decoder 124 is that the max-pooling operations in the encoder were replaced with up-sampling operations in the decoder, where the nearest-neighbor interpolation increases image size by a factor of 2 through each layer block. Because deconvolution uses random initialization and unequalled kernel size, which causes checkerboard artefacts, up-sampling is used for its replacement. Furthermore, the encoder 122 was connected to the decoder 124 through skip connections 124 at multi-scale resolution levels to help reconstruct the original spatial resolution levels to recover the original spatial resolution of the input T1-w image at the output. The features from each layer block in the encoder 122 were copied and concatenated with their corresponding ones in the decoder 124. These concatenations enable both high- and low-level features from the encoding part to be utilized as additional inputs in the decoding part to provide effective and stable image representation. The output layer of UNet in one embodiment of the present invention comprises a 1×1 convolutional layer and a stride of 1 followed by a hyperbolic tangent (tanh) activation function, which has been established to provide good results. The final layer reconstructs an output image from a 16-component vector of feature maps that has the same size as the input image (128×128×64).

Preprocessing

Before subjecting the image data to the AI engine of an embodiment of the present invention, the 3D-T1-w image was first resliced into the axial plane, changing its voxel size. To place the T1-w image in a single spatial coordinate system with its corresponding MRA, 3D-affine registration, which involves translation, center of mass, rigid body, and complete affine registration, is utilized to register 3D-volume of the T1-w images to MRA images.

In one embodiment of the present invention, this process is executed using DIPY (Diffusion imaging in Python) software library. An example of this process is illustrated in FIG. 2. In this example, the MRA image and T1-w image are indicated as static and moving, respectively. To obtain a maximum intensity projection (MIP)-MRA image from the MRA images, the AI engine executed by the system 100 used a publicly available software library, namely SimpleITK image analysis library found in GitHub (https://github.com/ljpadam/maximum_intensity_projection) to process the MRA images into 3D-MIP images. The T1-w, MRA, and MIP images were further normalized to obtain voxel intensity between 0 and 1 and resized to the same matrix size of (W×H×D)=128×128×64 using the spline interpolated zoom (SIZ) method.

Experimental Datasets

In one embodiment of the present invention, the system 100 is trained and tested using the IXI dataset which is publicly available on the web (https://brain-development.org/ixi-dataset/). The IXI dataset contains different MRI image modalities, including T1-w, T2-w, PD-w, DWI, and MRA images of normal, healthy subjects. In the experiment for training and testing the embodiments of the present invention, T1-w, and MRA image modalities were obtained. The datasets containing 522 subjects with paired T1-w and MRA images include 180, 316, and 26 datasets from Hammersmith Hospital (HH), Guys's Hospital (Guy), and the Institute of Psychiatry (IOP), respectively. Apart from the multi-institutional acquisition of the dataset, two types of scanners, 1.5 and 3 Tesla, and various imaging protocols were used to acquire the images. Notably, the T1-w images were acquired in the sagittal plane, and the MRA images were acquired in the axial plane with varying slice thicknesses. Furthermore, apart from IOP-based images with 1024×1024-pixel size and 92 slices, all other institutions have image dimensions of 512×512 pixels with 100 slices. The data were randomly divided into 70, 20, and 10% for training validation and testing set.

Model Training

In one embodiment of the present invention, the AI engine is configured with a UNet model 120 training a dataset with 512 3D images for the T1-w, MRA, and MIP images generated after pre-processing. The model trainable parameters were initialized using uniform distribution technique. The uniform distribution technique is shown to perform better than the Xavier technique in deep models with ReLU layers. In one embodiment, an adaptive optimizer such as the Adam stochastic optimization algorithm with a learning rate of 0.002 is applied to minimize a mean-squared error (MSE) loss function or L2 Loss function in a stepwise fashion and update the networks trainable at every training step progressively until the model reaches the convergence. MSE is used in the training as a cost function because it is computationally inexpensive and leads to a convex optimization problem with a stable gradient.

Figure 5:
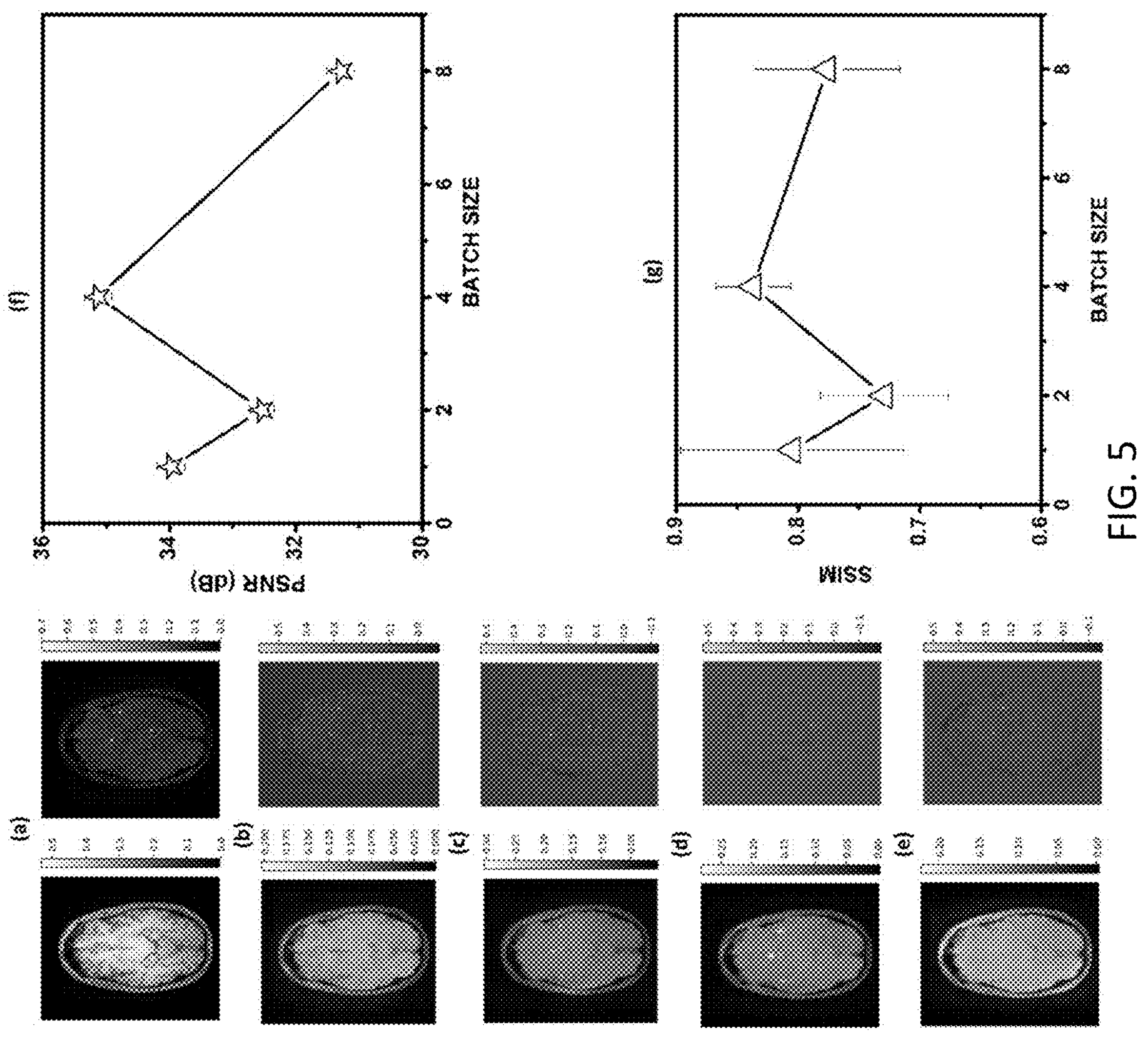
FIG. 5 illustrates various images, including (a) which is an illustration showing T1-w and MRA images used for an experiment for an embodiment of the present invention; (b) is an illustration showing synthesized MRA and corresponding difference map for a batch size of 1 in an experiment for an embodiment of the present invention; (c) is an illustration showing synthesized MRA and corresponding difference map for a batch size of 2 in an experiment for an embodiment of the present invention; (d) is an illustration showing synthesized MRA and corresponding difference map for a batch size of 4 in an experiment for an embodiment of the present invention; (e) is an illustration showing synthesized MRA and corresponding difference map for a batch size of 1 in an experiment for an embodiment of the present invention; (f) is an illustration showing a graphical representation of Peak signal-to-noise ratio (PSNR) of the synthesized MRA images from (a) to (e); (g) is an illustration showing a graphical representation of structural similarity index (SSIM) of the synthesized MRA images from (a) to (e)
Figure 6:
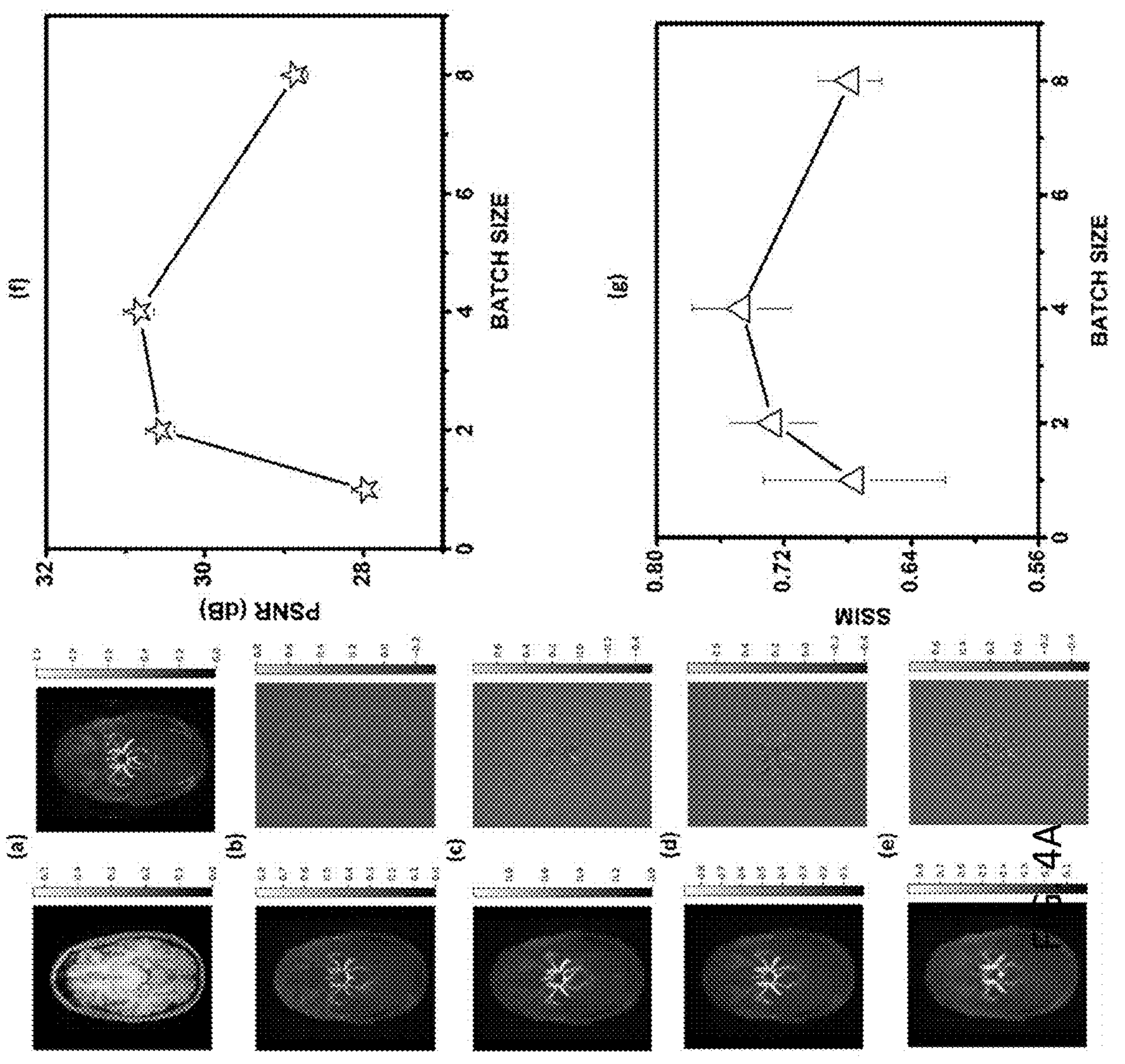
FIG. 6 illustrates various images, including (a) is an illustration showing T1-w and MIP images used for an experiment for an embodiment of the present invention; (b) is an illustration showing synthesized MIP and corresponding difference map for a batch size of 1 in an experiment for an embodiment of the present invention; (c) is an illustration showing synthesized MIP and corresponding difference map for a batch size of 2 in an experiment for an embodiment of the present invention; (d) is an illustration showing synthesized MIP and corresponding difference map for a batch size of 4 in an experiment for an embodiment of the present invention; (e) is an illustration showing synthesized MIP and corresponding difference map for a batch size of 1 in an experiment for an embodiment of the present invention; (f) is an illustration showing a graphical representation of Peak signal-to-noise ratio (PSNR) of the synthesized MIP images from (a) to (e); (g) is an illustration showing a graphical representation of structural similarity index (SSIM) of the synthesized MIP images from (a) to (e)
Figure 7:
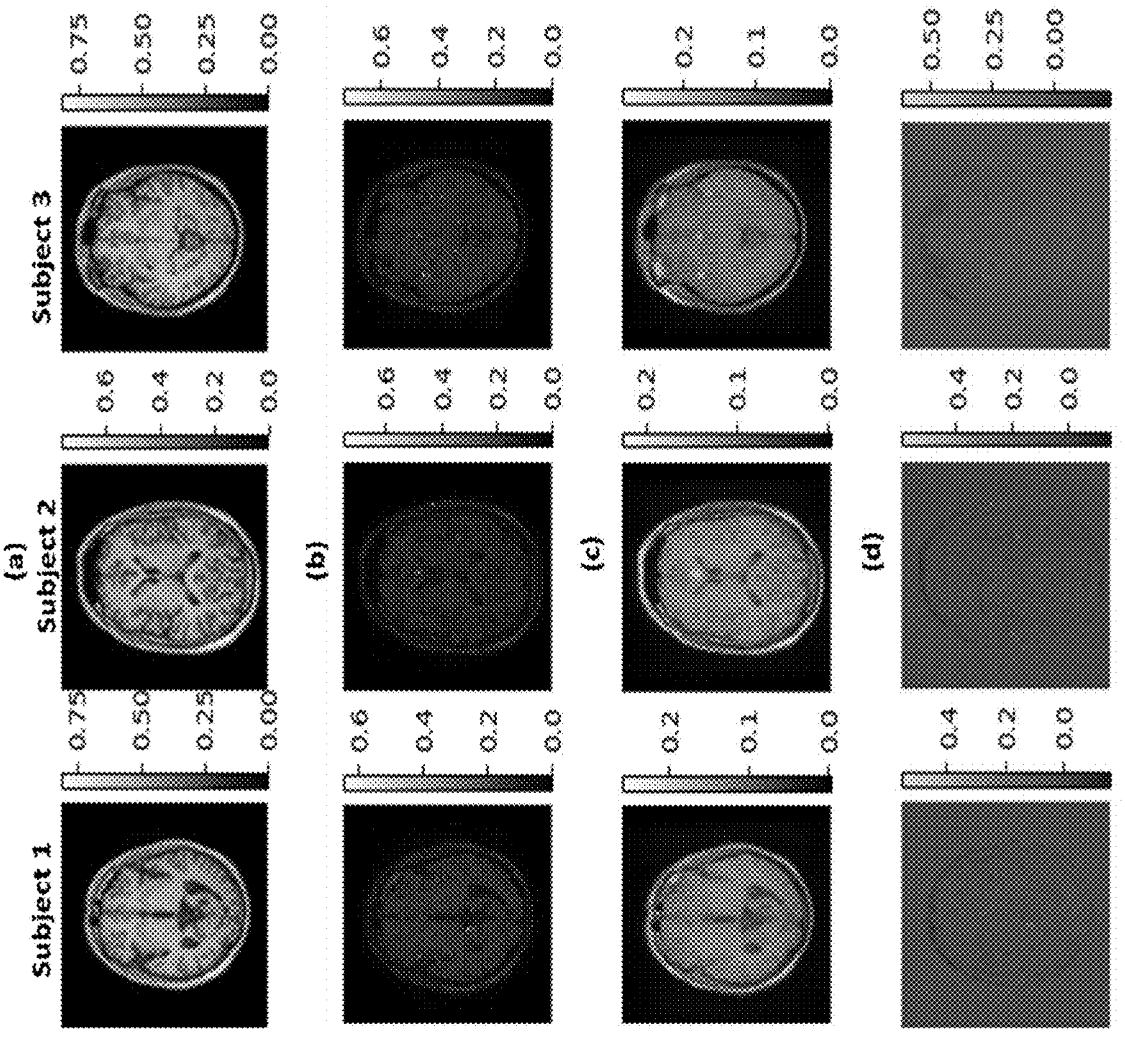
FIG. 7 includes a set of visualizations of three-subject testing of the proposed model, including (a) is a set of visualizations of three-subject testing of the proposed model on the translation of T1 w to MRA showing 2D axial middle slice of T1-w images in one embodiment of the present invention; (b) is a set of visualizations of three-subject testing of the proposed model on the translation of T1 w to MRA showing 2D axial middle slice of ground truth MRA images in one embodiment of the present invention; (c) is a set of visualizations of three-subject testing of the proposed model on the translation of T1 w to MRA showing 2D axial middle slice of synthesized MRA images in one embodiment of the present invention; (d) is a set of visualizations of three-subject testing of the proposed model on the translation of T1 w to MRA showing 2D axial middle slice of difference map between the synthesized and ground truth MRA in one embodiment of the present invention.

In the present invention, the end-to-end 3D U-Net architecture model 100 for the T1-w to MRA translation resulted in 2 million trainable parameters. These parameters were optimized during the model training on the training data set to learn how to map a source T1-w image to a target MRA or MIP contrast as shown in FIG. 5. Referring to FIG. 4, the 3D U-Net architecture model 120 was trained to perform the possible translation which involves translating T1-w images to MRA before obtaining the MIP to reveal the vascular trees. Also, the same model will be trained to synthesize MIP directly from T1-w images using an embodiment of the present invention. Referring to FIG. 5 and FIG. 6 which show the result of the experiments for training and testing one embodiment of the present invention, the batch size, defined as the number of samples per gradient update, was set to 1, 2, 4, and 8 to investigate the batch size that gives the best performance, during which the model was trained for 100 epochs. Furthermore, the effect of using 10 times the initial number of epochs to establish the model performance between the underfitting and overfitting stages was examined.

Model Evaluation

In an experiment performed using the system 100 of an embodiment of the present invention, residuals or difference maps are computed using the formula $(x_i, y_i)=y_i-x_i$ to compare the synthesized MRA and MIP images along with visual comparison. The quality of the synthesized MRA and MIP images with U-Net was evaluated against the ground-truth images using two voxel-wise metrics, which are built using the pixel-wise metrics across the image depth: peak signal-to-noise ratio (PSNR) and structural similarity index (SSIM) metric. These metrics, widely used to assess overall quality while capturing features dominated by lower spatial frequencies, consider the quantitative and qualitative differences that mimic human perception. The PSNR, which takes into account both the MSE and the highest possible intensity value of the image, is defined as $$PSNR(x, y) = 10 \times \log_{10}\left(I^2_{max}/MSE\right),$$

where $$I^2_{max}$$

is the maximum pixel value of the image that depends on the data type. SSIM captures the human-perceived quality of the synthesized image by comparing two images. Its formula is given as:

$$SSIM(x, y) = \frac{(2\mu_x\mu_y + C_1)(2\sigma_{xy} + C_2)}{\left(\mu_x^2 + \mu_y^2 + C_1\right)\left(\sigma_x^2 + \sigma_y^2 + C_2\right)},$$

where $\mu$ is the mean image intensity, $\sigma^2$ is the variance of the image, $\sigma_{xy}$ is the covariance of the ground-truth (x) and predicted (y) images and $C_1$ and $C_2$ are constants added to stabilize the division with a weak denominator. However, from the experiment conducted using the system 100 of an embodiment of the present invention, an average ±SEM of the PSNR and SSIM across all the validation datasets is observed.

Batch Size Effect on Model Performance

The result obtained from using different batch sizes for training the proposed model in the translation of T1 weighted images to MRA images is shown in FIG. 5(*a-e*). Using the difference map, the 2D axial slices of the synthesized MRA are compared to the corresponding ground truth MRA slices. However, variations were observed with the change in batch size regarding two significant features, including tiny vascular features (white dots) and the image contrast. Compared to other batch sizes, MRA images obtained from batch size 8 show no vascular features. Quantitative analysis shows the PSNR (FIG. 5(*f*)) and SSIM (FIG. 5(*g*)) of the synthesized MRA changes with a change in batch size. However, batch size 4 exhibits the best result with the highest PSNR and SSIM. The lowest PSNR and SSIM were obtained with batch sizes of 8 and 2, respectively. Hence, the image batch size of 4 remains the best in getting an excellent result while training the model for translating T1-weighted images to MRA.

Visual appearance of the 2D axial slices obtained from synthesized MIP and the ground truth MIP with different batch sizes were inspected and compared to determine the optimized batch size for translating T1w to MIP using the UNet model 120 of an embodiment of the present invention. The difference maps and MIP images are shown in FIG. 6(*a-e*). A close similarity in the vascular trees was observed at low resolution. However, the vascular tree's sharpness and continuity vary with the batch size.

Comparing to other batch sizes, the images with the worst sharpness are found with a batch size of 8. In addition, quantitative analysis with PSNR (FIG. 6(*f*)) and SSIM (FIG. 6(*g*)) was obtained between the synthesized MIP and ground truth MIP. The PSNR, with different batch sizes, is found to vary in the same order as the SSIM, namely Batch Size 1<8<2<4. The batch size of 4 generates the best result with the highest PSNR and SSIM, while the lowest value is observed with a batch size of 1. Hence, for translating T1 w images to MIP and T1 w images to MRA, the image batch size 4 remains the best choice in training the proposed model.

Figure 8:
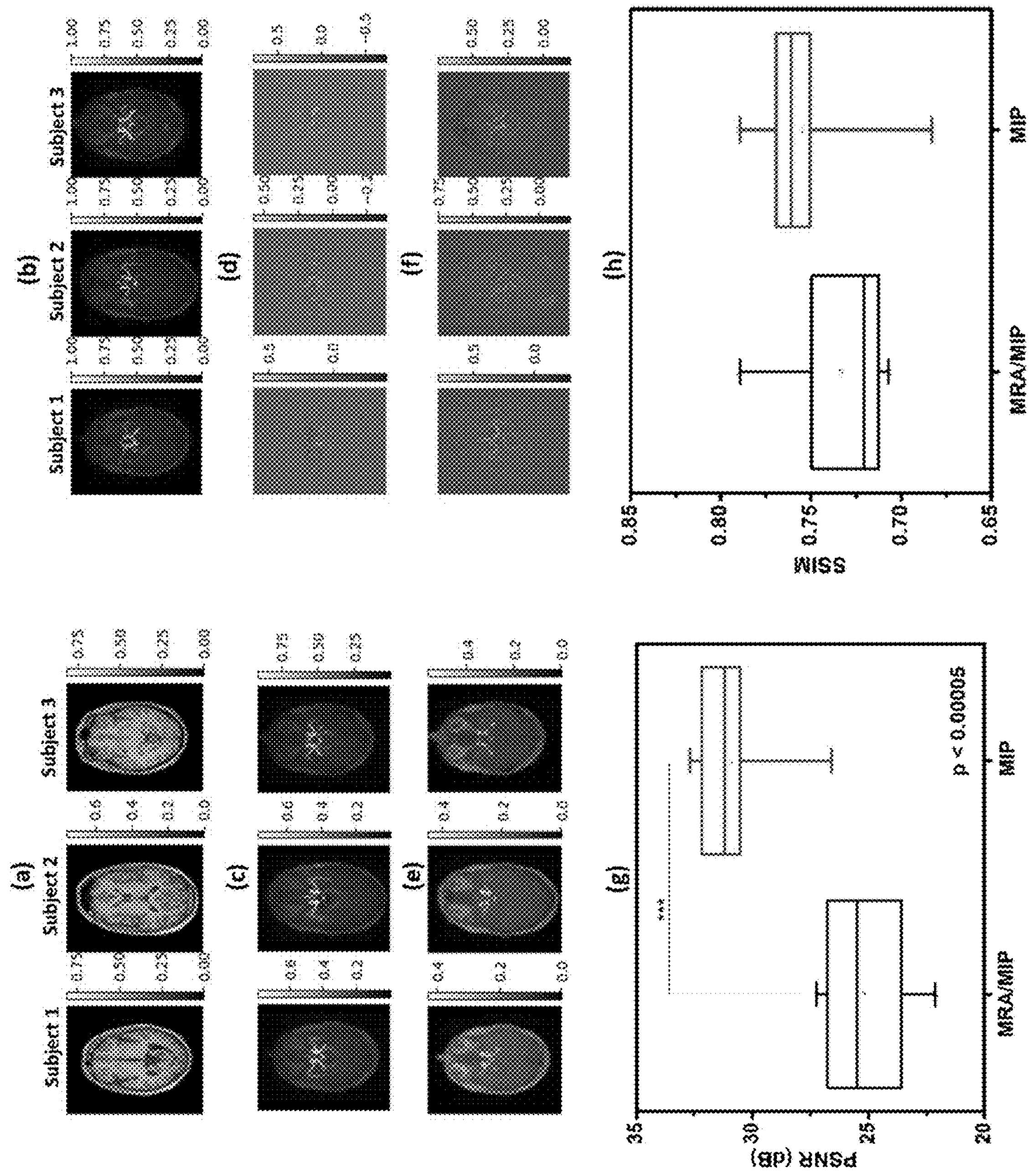
FIG. 8 is a set of visualizations of three-subject testing of the proposed model including (a) is a set of visualizations of three-subject testing of the proposed model on the translation of T1-w to MIP and MRA MIP showing 2D-axial middle slice of T1-w images in one embodiment of the present invention; (b) is a set of visualizations of three-subject testing of the proposed model on the translation of T1-w to MIP and MRA MIP showing 2D-axial middle slice of ground truth MIP images in one embodiment of the present invention; (c) is a set of visualizations of three-subject testing of the proposed model on the translation of T1-w to MIP and MRA MIP showing 2D-axial middle slice of synthesized MIP images in one embodiment of the present invention; (d) is a set of visualizations of three-subject testing of the proposed model on the translation of T1-w to MIP and MRA MIP showing 2D-axial middle slice of difference maps between the synthesized and ground truth MIP images in one embodiment of the present invention; (e) is a set of visualizations of three-subject testing of the proposed model on the translation of T1-w to MIP and MRA MIP showing 2D-axial middle slice of synthesized MRA/MIP images in one embodiment of the present invention; (f) is a set of visualizations of three-subject testing of the proposed model on the translation of T1-w to MIP and MRA MIP showing 2D-axial middle slice of difference maps between the synthesized MRA/MIP and ground truth MIP in one embodiment of the present invention; (g) is a set of visualizations of a box plot comparing the average PSNR between the MIP and MRA/MIP in one embodiment of the present invention; (h) is a set of visualizations of a box plot comparing the average SSIM between the MIP and MRA/MIP. In one embodiment of the present invention.

In one embodiment of the present invention, the UNet model 120 has a batch size set to 4 in translating T1w to MRA images across multiple subjects. Reference is now made to FIG. 8. The T1w (FIG. 8(*a*)) and ground truth MRA (FIG. 8(*b*)) for three different subjects were compared with the synthesized MRA (FIG. 8(*c*)) to obtain the difference map (FIG. 8(*d*)). The variation in the T1w images was maintained in the synthesized MRA with variations in tiny vascular features. Hence, the MRA synthesis of the model is sensitive to the anatomical variation in the T1-w image, with more vascular features observed in subject 3.

In one embodiment of the present invention, the UNet model 120 has a batch size set to 4 in translating T1w to MIP images across multiple subjects. The T1-w (FIG. 8(*a*)) and ground truth MIP (FIG. 8(*b*)) for three different subjects were employed for comparison with the synthesized MIP (FIG. 8(*c*)) and MRA/MIP images (FIG. 8(*e*)) to obtain their corresponding difference map shown in FIGS. 8(*d*) and (*f*) respectively. The anatomical variation created a structural variation in the vascular tree and vascular features can be observed in the synthesized MIP and MRA/MIP. Hence, the synthetic ability of the model is sensitive to the anatomical variation in the T1-w images. In addition, more vascular features emerge in the synthesized MIP than in the MRA/MIP. Furthermore, quantitative analysis shows that synthesized MIP has a statistically significantly higher PSNR and SSIM than MRA/MIP, as demonstrated in FIGS. 8(*g*) and (*h*).

Effect of Extended Training Steps on the Performance of the Proposed Model

Figure 9:
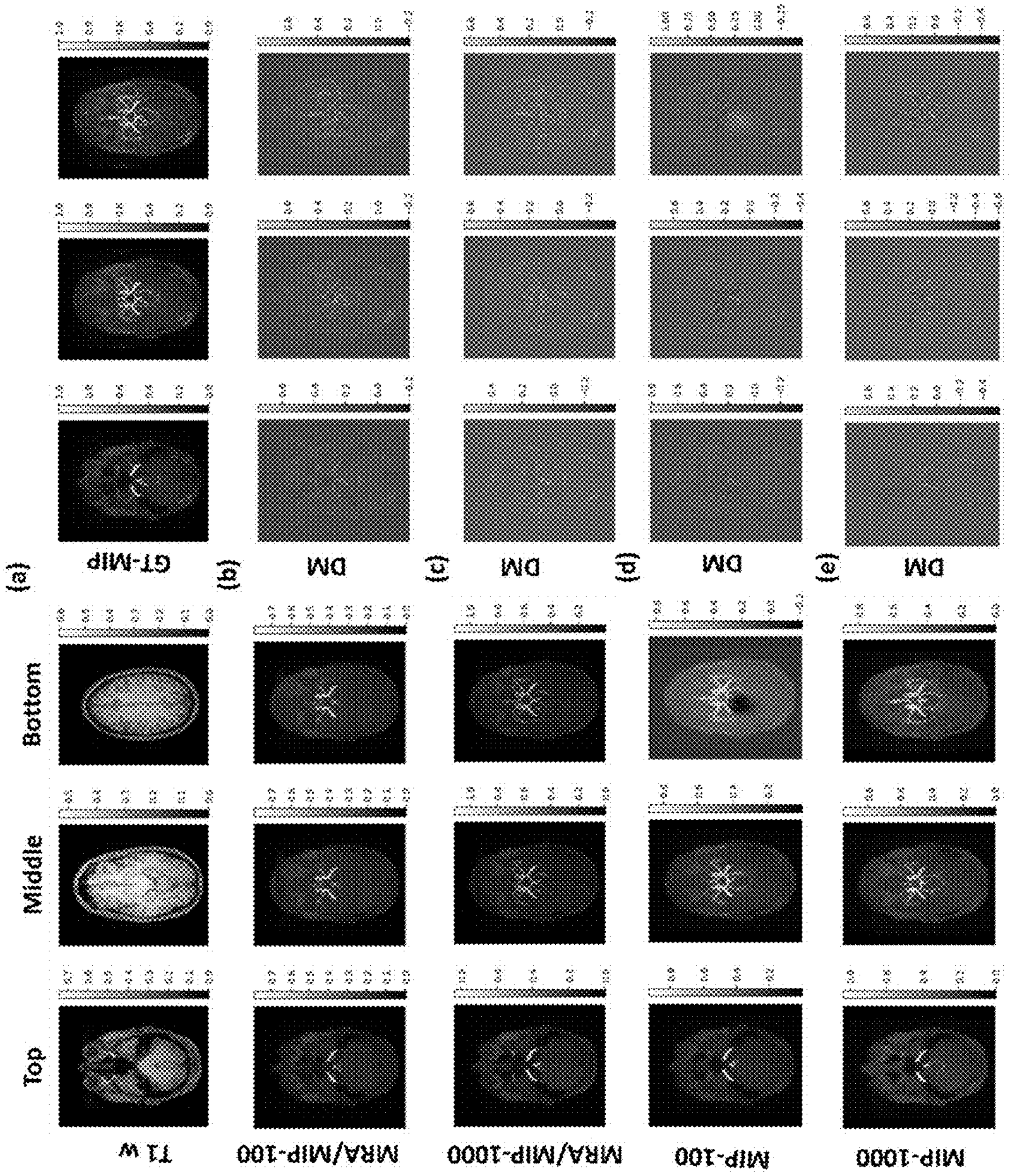
FIG. 9 is a set of visualizations, including (a) is a set of visualizations of T1-w images and corresponding ground truth MIP images in one embodiment of the present invention; (b) is a set of visualizations of MRA/MIP images and difference maps at 100 epochs in one embodiment of the present invention; (c) is a set of visualizations of MRA/MIP images and difference maps at 1000 epochs in one embodiment of the present invention; (d) is a set of visualizations of MIP images and difference maps at 100 epochs in one embodiment of the present invention; (e) is a set of visualizations of MIP images and difference maps at 1000 epochs in one embodiment of the present invention.

Using MRI scanned from a single subject, the system 100 of the present invention is adapted to synthesize MIP and MRA/MIP with the vascular tree at different depths, namely the top, middle and bottom axial slices, as illustrated in the T1-w images of FIG. 9. The UNet model of the present invention is trained for 1000 epochs and the resulting images are compared with those obtained at 100. The depth-wise analysis shows that the vascular tree's additional features were added to the vascular tree of the synthesized MIP and MRA/MIP after 1000 epochs. In detail, the well-developed top and the middle slices were maintained, and the deprecated features at the bottom slices became well vascularized for the synthesized MIP. In addition, a slight improvement in the vascular tree was observed at the middle and bottom slices for MRA/MIP. However, the features are more numerous for MIP than MRA/MIP. Hence, training the model for a more extended number of epochs improves the vascular tree. Furthermore, vascular sharpness was enhanced, but vascular discrepancies, including vessel gaps, were presented in the difference map.

Figure 10:
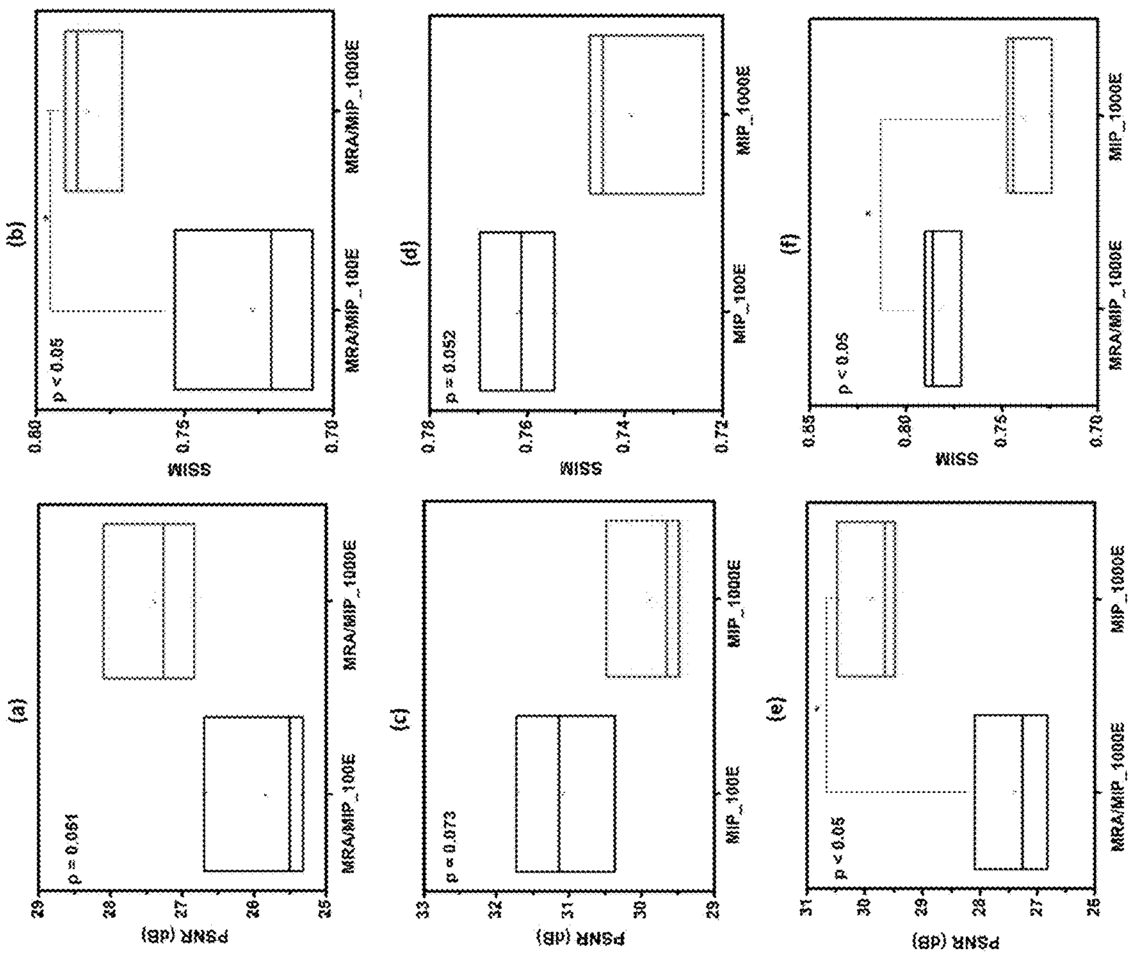
FIG. 10 illustrate a set of diagrams which includes (a) is a diagram showing a box plot comparing PSNR between MRA/MIP at 100 epochs and 1000 epochs; (b) is a diagram showing a box plot comparing PSNR between MIP at 100 epochs and 1000 epochs; (c) is a diagram showing a box plot comparing PSNR between MRA/MIP and MIP at 1000 epochs; (d) is a diagram showing a box plot comparing SSIM between MRA/MIP at 100 epochs and 1000 epochs; (e) is a diagram showing a box plot comparing SSIM between MIP at 100 epochs and 1000 epochs; (f) is a diagram showing a box plot comparing (c) SSIM between MRA/MIP and MIP at 1000 epochs.
Figure 11:
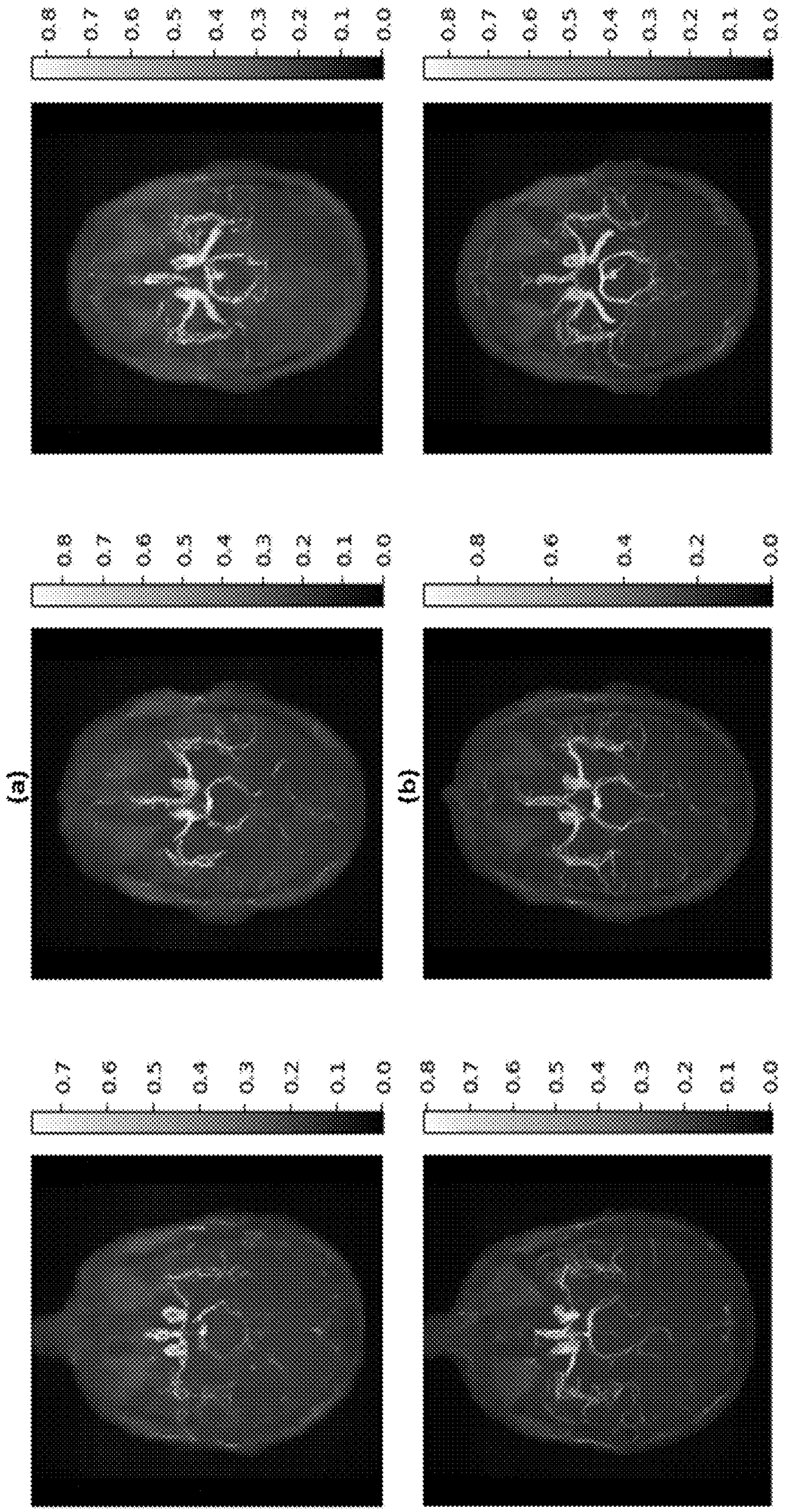
FIG. 11 are plots which include (a) is a plot showing detection accuracies on cross-modal image detection, wherein the models are trained on TCG and tested on GAN; (b) is a plot showing detection accuracies on cross-modal image detection, wherein the models are trained on TCG and tested on DM; (c) is a plot showing detection accuracies on cross-modal image detection, wherein the models are trained on DM and tested on GAN; and (d) is a plot showing detection accuracies on cross-modal image detection, wherein the models are trained on GAN and tested on DM.

The quantitative involving the PSNR and SSIM describing the effect of the extended training step is shown in the box plots of FIG. 10(*a-f*). Metric changes observed after 100 epochs include (i) enhancement in the PSNR for MRA/MIP, (iii) statistically significant improvement in the SSIM of MRA/MIP, (ii) a reduction in the PSNR and SSIM for synthesized MIP. Furthermore, between MRA/MIP and MIP at 100 epochs, there is a statistically significant decrease in the PSNR and a decrease in the SSIM. Hence, a longer training step has an improvement in the PSNR of the MRA/MIP but not well enough to nullify the difference with that of the MIP, and it also has a negative impact on the SSIM of the MIP. Further investigation was done by increasing the voxel size of the images to 256×256×64 for our direct translation approach. The MIP obtained after voxel increment (FIG. 10(*a-b*)) shows an improved image quality and more improved vessel anatomy compared with the 128×128×64 voxel.

From a magnetic resonance image synthesis perspective, the system 100 of an embodiment of the present invention comprises a processor to execute an AI engine configured to a UNet model 120 to synthesize vascular anatomical trees from routine T1-w image scans. The present invention reduces the need for multi-contrast MR images to acquire MRA images because reducing the MR contrast image to the earliest acquired image in MRI scans can also contribute to the decreasing time objective. Also, the system 100 is designed to reconceptualize developing a synthetic MRA image before achieving a vascular tree through maximum intensity projection. Furthermore, the UNet 120 of an embodiment of the present invention is adapted to exploit the approach of using a stable model with lesser tuneable parameters and computational cost.

In one embodiment of the present invention, the optimal batch size of 4 is recommended to use for real world implementation. The UNet architecture model's sensitivity to synthesizing MRA and MIP from T1-w images of subjects exhibiting different anatomical structures at the same axial slice position, such as consecutive MRA images which differed in the same manner as the input images. In addition, the obtained and synthesized MIPs show different root structures for the vascular trees.

The experimental results demonstrate the capability of UNet model 120 for predicting vascular features directly from 3D T1-w images. Visual comparison of the vascular images revealed that the synthetic MIP resembled the ground truth MIP. This similarity decreases as the vessel diameter decreases because of the low-resolution inputs used for training the system 100.

However, after training the model for 100 epochs, it is observed that the vascular trees in the MRA/MIP are not fully developed. This indicates that either a longer training step will be required, or a more complex architecture may be required.

In testing an embodiment of the present invention, the vascular trees acquired through MRA/MIP are compared with those of direct MIP. It is observed that multiple features like image contrast, brightness and the presence of tiny vascular features are essential in generating the vascular trees. The vascular trees are one of the essential factors for the training of an embodiment of the present invention. Nonetheless, after training the model for 1000 epochs, it is observed that a lot of smaller vessels missing in the vascular trees of the MRA/MIP compared to the synthesized MIP. This supports that a more complex AI model is required, or a longer training step is required to improve the efficiency of an embodiment of the present invention. The compared average PSNR values in FIGS. 5 to 10 also support this.

The experimental results along with the quantitative analysis of an embodiment of the present invention showed that the present invention is capable of identifying more branches of smaller vessels in vascular trees than the existing approaches. The assessment of the present invention reveals that the quality of the vasculature generated by the embodiment of the present invention is sensitive to anatomical changes and the quality of the T1-w image. Hence, the present invention provides the potential to remove the bottlenecks involved in generating digital twin of MIP version of MRA images from one or more structural MR images while reducing patient waiting time for diagnosis.

In one embodiment of the present invention, there is provide a system 10 relates to the maximum intensity projection (MIP) of magnetic resonance angiography (MRA) for magnetic resonance imaging (MRI). The system 10 is adapted to provide a simulated MIP image from a T1-weighted image input without contrast agents. The present invention has tremendous industry applications in hospitals, radiological centers, and research institutes. These applications includes, but not limited to:

(i) Disease diagnosis: The non-invasive imaging of blood vessels in the brain;

(ii) Rapid treatment monitoring: The monitoring of changes in brain vasculatures after treatment of cerebrovascular disease in patients;

(iii) Scientific discovery: scientist and research groups can use this technology to discover new treatment paradigms and better understand underlying cerebrovascular mechanism.

Some advantages of embodiments of the present invention over existing technologies include:

(i) It involves no contrast agent compared to the contrast-enhanced MRA-MRI system[5]

(ii) It offers a fast generation (within a few seconds) of MIP images and no concern over patient motion effect[6] on generated images compared to a non-contrast MRI-MRA system.

(iii) iii. Compared to existing technologies generating MRA from single or multi-non-contrast images using deep learning, it does not involve the use of advanced MIP generative software, which sometimes provides disjointed vasculatures due to variation in image contrast and brightness.

(iv) It directly generates the brain vascular tree.

(v) It provides a cheap means of cerebrovascular disease diagnosis. vi. It is readily available and can be incorporated into any portable device for easy access.

Embodiments of the present invention may provide a novel and inventive technique that combines image processing technology NIFTI formatting (Neuroimaging informatics technology initiative), deep learning, and artificial intelligence, to process selected inputs which were obtained without the use of contrast agent from which it generates maximum intensity projection (MIP) images of magnetic resonance angiography (MRA) images for the diagnosis or treatment monitoring of various cerebrovascular diseases without the use of harmful contrast agents.

Figure 12:
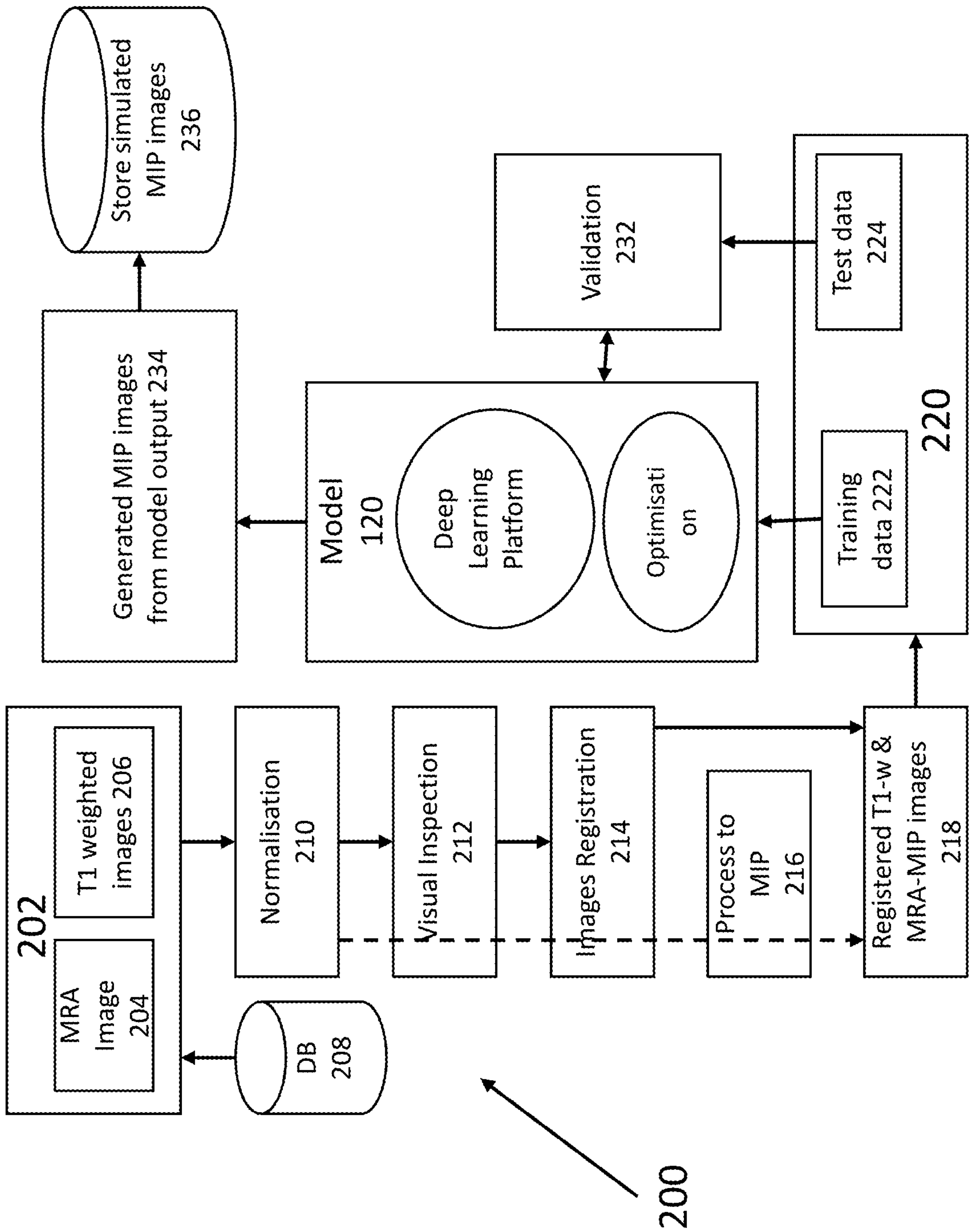
FIG. 12 is a block diagram illustrating the workflow steps and components of the method of an embodiment of the present invention including the model training and validation.

Referring to FIG. 12 is a block diagram illustrating the workflow steps and components of the method 200 in accordance with another embodiment of the present invention. In this embodiment, the method 200 comprises the steps of:

(i) Collecting a single non-contrast (SNC) image 204 and corresponding MRA images 206 from the database 208 in step 202.

(ii) Pre-processing the collecting images through visual inspection 212, voxel normalization 210 and template registration 214 & 218 in the pre-processing module.

(iii) Postprocessing the MRA images into MIP images 216.

(iv) Storage of the MIP images and corresponding SNC images in the input module in step 220.

(v) Separation of the image pairs into a series of training and test data 224. Input the SNC images and corresponding MIP images 222 into the model 226 of the training module.

(vi) In the training module 226, the model 120 is trained to learn the generation of simulated MIP images in step 234 upon the use of the SNC image as the model input and the simulated MIP image as the target output. The tunable parameters of the model are adjusted so that the output images generated by the model are optimized to be analogous to the training data targets.

(vii) Testing the simulated MIP images against the corresponding MIP images previously input into the model 120, which is standard to validate the model in the validation module 232.

(viii) The generated simulated MIP images are then step in the database 208 in step 236.

Figure 13:
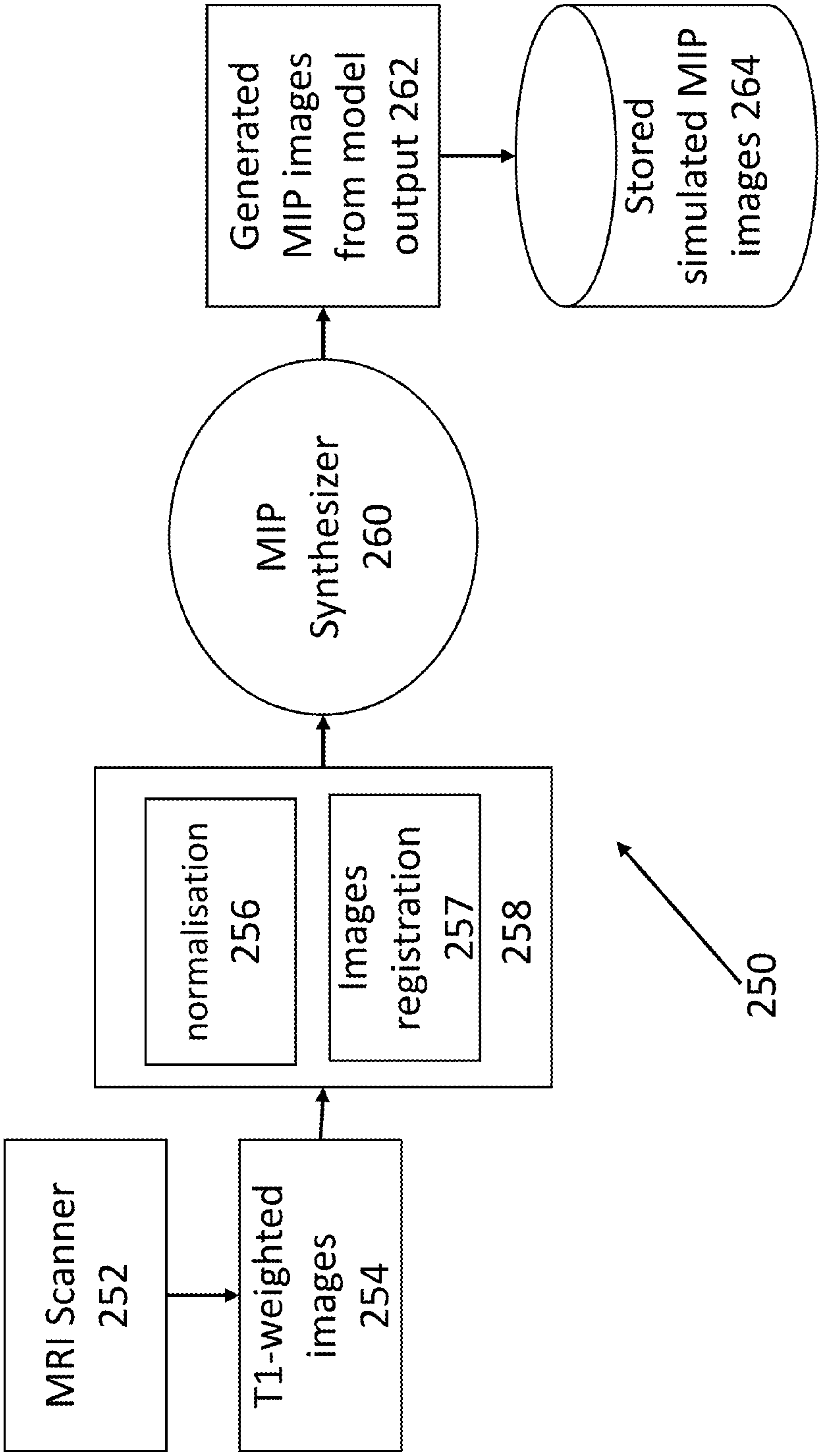
FIG. 13 is a block diagram illustration of routine steps of the method of an embodiment of the present invention to generate simulated MIP images from T1 weighted images.

FIG. 13 describes the method 250 of an embodiment of the present invention to generate simulated MIP images from T1 weighted images. The method 250 comprising the steps of:

(i) The SNC images 254 collected in NIFTI format from the MRI scanner in the step 252 are transferred into the input module.

(ii) In step 258, the system 199 pre-processing the SNC images through template registration 257 and voxel normalization 256.

(iii) Transfer the SNC images into the trained model 120, which accepts SNC images as input in step 260 and provides MIP images 262 as output.

(iv) Transfer the generated to a medical archiving or store it in an output storage module in step 264.

In another embodiment of the present invention, there is provided a system 100 for executing the method for generating a simulated MIP image of a patient's brain based upon a single non-contrast (SNC) MR image of the brain without injection of a contrast agent into the brain. The method comprises the steps of:

(i) An input image module to store SNC images of the patient's brain.

(ii) A pre-processing module adapted to receive the SNC image, prepare and generate into the standard required for the model to extract and understand its features effectively.

(iii) A simulated MIP-generating model compartment adapted to receive the patient's SNC images and to generate fake MIP images corresponding to each SNC image.

(iv) A deep learning platform arranged and structured to operate the connected model.

(v) A training module that receives and communicates the training data to the deep learning platform whereby tunable parameters of the model may be adjusted to optimize the simulated MIP images (vi) A testing module that communicates with the training module and the deep learning platform to receive testing data whereby pre-trained performance criteria validate the simulated MIP images generated by the model (vii) An output storage compartment adapted to receive the simulated MIP images generated by the model.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilized. This will include edge computing devices, stand-alone computers, network computers, cloud-based computing devices and dedicated hardware devices. Where the terms "computing system" and "computing device" are used, these terms are intended to cover any appropriate arrangement of computer hardware capable of implementing the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A method for synthesizing MRA and MIP of MRA images using acquired single contrast MR image (T1-w MR image) by a system having at least a processor and a memory therein to execute instructions of an artificial intelligence engine configured to a UNet model stored within the memory of the system; wherein the UNet model comprises:

an encoder having a plurality of layer blocks, each of the layer blocks of the encoder comprising one or more convolutional layers, each of the convolution layers associating with an activation layer, and a down sampling layer;

a decoder having a plurality of layer blocks, each of the layer blocks of the decoder comprising one up-sampling layer, one or more convolutional layers, and each of the convolution layers associating with an activation layer;

a skip connection for associating with one of the layer blocks of the encoder with one of the layer blocks of the decoder at a corresponding multiscale resolution level;

wherein the encoder is adapted to extract features from the T1-w MR image for the decoder to combine outputs from the encoder and extracted image features in multiscale resolution levels through the skip connection to generate the MRA and MIP of MRA images, wherein one or more convolution layers within the decoder use random initialization and unequalled kernel size.

2. The method of claim 1, wherein the decoder comprises an output layer to generate an image with a same resolution as the input image.

3. The method of claim 2, wherein the output layer comprises a single output convolutional layer followed by an output activation layer.

4. The method of claim 3, wherein the single output convolutional layer is a 1×1 convolutional layer with a stride of 1.

5. The method of claim 4, wherein the output activation layer is adapted to conduct hyperbolic tangent (tanh) operations.

6. The method of claim 1, wherein the encoder and the decoder are adapted to perform cross-sequence from a T1-w image to MRA or MIP image translation consisting of 19 convolutional layers.

7. The method of claim 1, wherein the encoder is adapted to receive images comprising three dimensions and one or more color channels.

8. The method of claim 1, wherein one or more layer blocks of the encoder comprises a repeated implementation of two 3×3 convolution layers with 2 voxels stride over five-layer blocks.

9. The method of claim 1, wherein a layer block of the encoder that immediately precedes the decoder comprises a single convolution layer.

10. The method of claim 1, wherein a zero padding technique is implemented before each convolution layer.

11. The method of claim 1, wherein the activation layer is adapted to conduct a linear rectification function by one or more rectified linear units (ReLU).

12. The method of claim 1, wherein the down sampling comprises a 2×2×2 max-pooling operation with a stride of 2 voxels.

13. The method of claim 1, wherein each of the convolutional layers is adapted to process input data with a number of convolutional filters.

14. The method of claim 1, wherein the number of convolutional filters is doubled from a first layer block to a last layer block within the encoder.

15. The method of claim 1, wherein the up-sampling layer of the decoder is adapted to perform nearest-neighbor interpolation to increase image size through each layer block within the decoder.

16. The method of claim 1, wherein the skip connection is adapted to copied and concatenated features generated from one of the layer blocks of the encoder to one of the layer blocks of the decoder at a corresponding multiscale resolution level.

17. The method of claim 1, wherein the UNet model is trained with a batch size of 4.

18. The method of claim 1, wherein the UNet model is trained with consecutive MRA images which differed in a same manner as input images, and is trained with over 100 epochs.

19. A system for deep learning-based translation of T1-weighted image to vasculature image of a brain comprising: a memory to store instructions and a processor to execute instructions stored within the memory; the processor to execute an artificial intelligence engine configured to a UNet model stored within the memory of the system; wherein the UNet model comprising:

an encoder having a plurality of layer blocks, each of the layer blocks of the encoder comprising one or more convolutional layers, each of the convolution layers associating with an activation layer, and a down sampling layer;

a decoder having a plurality of layer blocks, each of the layer blocks of the decoder comprising one up-sampling layer, one or more convolutional layers, and each of the convolution layers associating with an activation layer;

a skip connection for associating with one of the layer blocks of the encoder with one of the layer blocks of the decoder at a corresponding multiscale resolution level;

wherein the encoder is adapted to extract features from the T1-w MR image for the decoder to combine outputs from the encoder and extracted image features in multiscale resolution levels through the skip connection to generate the MRA and MIP of MRA images, wherein one or more convolution layers within the decoder use random initialization and unequalled kernel size.

* * * * *